United States Patent [19]
Dumitrescu et al.

[11] Patent Number: 6,123,205
[45] Date of Patent: Sep. 26, 2000

[54] SAMPLE TUBE RACK

[75] Inventors: Nicolae Dumitrescu, Stamford; Irena Makarchuk, Fairfield, both of Conn.

[73] Assignee: Bayer Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/978,715

[22] Filed: Nov. 26, 1997

[51] Int. Cl.[7] ...................................................... A47F 7/00
[52] U.S. Cl. ............................ 211/74; 211/60.1; 422/104; 422/102; 422/100; 206/443
[58] Field of Search .................... 211/74, 60.1; 422/104, 422/101, 102, 71; 206/443, 201, 100; D24/227, 229, 230

[56] References Cited

U.S. PATENT DOCUMENTS

| | | | |
|---|---|---|---|
| D. 413,391 | 8/1999 | Lapeus et al. ........................... | D24/227 |
| 1,549,111 | 8/1925 | Grollman ............................... | 211/74 X |
| 1,634,953 | 7/1927 | McCune et al. ......................... | 422/104 |
| 1,980,930 | 11/1934 | Reyniers .................................. | 211/74 |
| 2,467,873 | 4/1949 | Weir ....................................... | 211/74 |
| 2,708,037 | 5/1955 | Planeta ..................................... | 211/74 |
| 2,741,913 | 4/1956 | Dovas ...................................... | 73/61 |
| 2,956,686 | 10/1960 | Garey ....................................... | 211/74 |
| 2,979,210 | 4/1961 | Patterson .................................. | 211/74 |
| 3,109,084 | 10/1963 | Walsh ..................................... | 211/74 X |
| 3,186,556 | 6/1965 | Frosstrom ................................ | 211/74 |
| 3,286,583 | 11/1966 | Ferrari ..................................... | 88/14 |
| 3,551,062 | 12/1970 | Brown .................................... | 356/246 |
| 3,698,563 | 10/1972 | Gordon et al. ....................... | 211/60.1 X |
| 3,765,538 | 10/1973 | Kowert ................................... | 211/60.1 |
| 3,905,482 | 9/1975 | Knulst ..................................... | 211/74 |
| 4,142,633 | 3/1979 | Raghavachari et al. ............ | 206/443 X |
| 4,207,289 | 6/1980 | Weiss ................................... | 211/74 X |
| 4,422,555 | 12/1983 | Jacobs ..................................... | 211/74 |
| 4,510,119 | 4/1985 | Hevey .................................. | 211/74 X |
| 4,534,465 | 8/1985 | Rothermal et al. ..................... | 206/443 |
| 4,895,650 | 1/1990 | Wang .................................. | 422/101 X |
| 5,080,232 | 1/1992 | Leoncavallo et al. .............. | 206/443 X |
| 5,137,693 | 8/1992 | Mawhirt ................................. | 422/104 |
| 5,141,117 | 8/1992 | Olsen et al. ......................... | 211/74 X |
| 5,186,339 | 2/1993 | Heissier ................................... | 211/74 |
| 5,378,433 | 1/1995 | Duckett et al. .................... | 211/60.1 X |
| 5,525,304 | 6/1996 | Matsson et al. ....................... | 422/104 |
| 5,672,317 | 9/1997 | Buhler . | |
| 5,959,221 | 9/1999 | Boyd et al. ....................... | 422/104 X |

FOREIGN PATENT DOCUMENTS

| | | |
|---|---|---|
| 0 753 747 A2 | 1/1997 | European Pat. Off. . |
| 92 06 037 U | 10/1992 | Germany . |

*Primary Examiner*—Daniel P. Stodola
*Assistant Examiner*—Khoa Tran
*Attorney, Agent, or Firm*—Andrew L. Klawitter, Esq.; Rodman & Rodman

[57] ABSTRACT

A sample rack for holding sample tubes in a single row includes an angle shaped frame formed by a longitudinally extending vertical rear wall and a horizontal top wall. The top wall includes a plurality of sample tube openings. A plurality of vertical partitions are joined to the angle shaped frame in spaced arrangement to define sample tube chambers for receiving sample tubes. At least one front vertical connecting section connects the bottom portions of two adjacent partitions opposite the rear wall. A leaf spring device is attached to the connecting section. The leaf spring device includes a support section and a plurality of arms opposite the rear wall extending upwardly from the support section into the sample tube chambers.

15 Claims, 6 Drawing Sheets

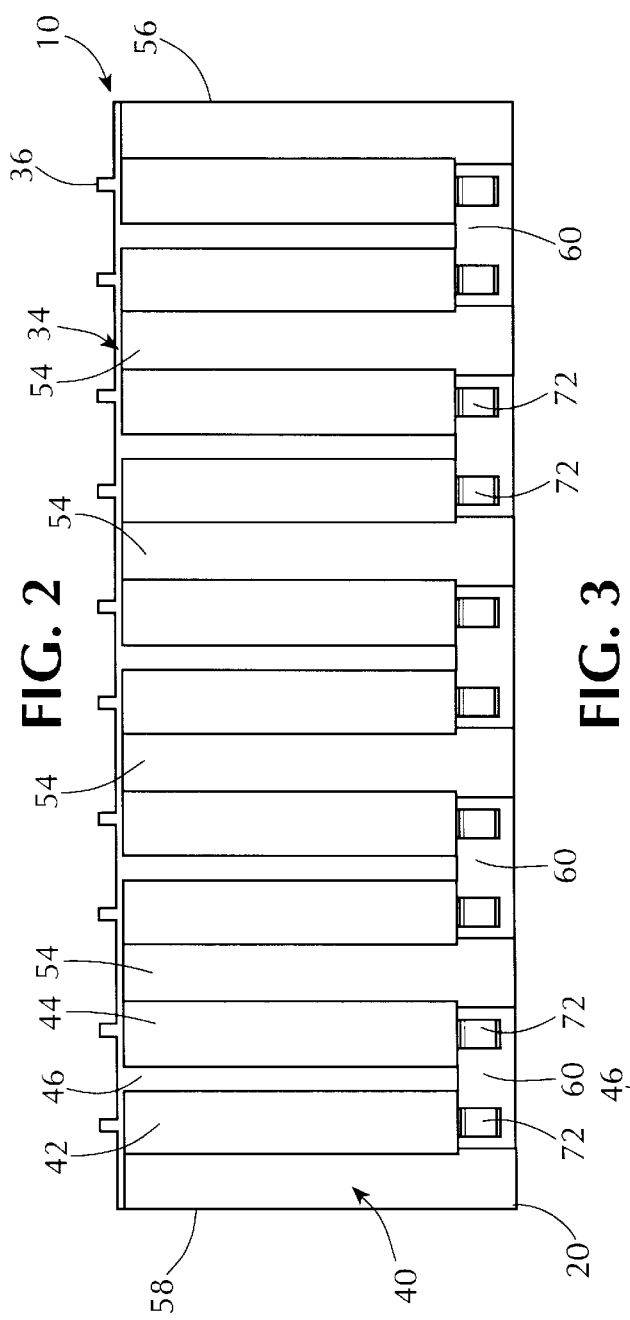
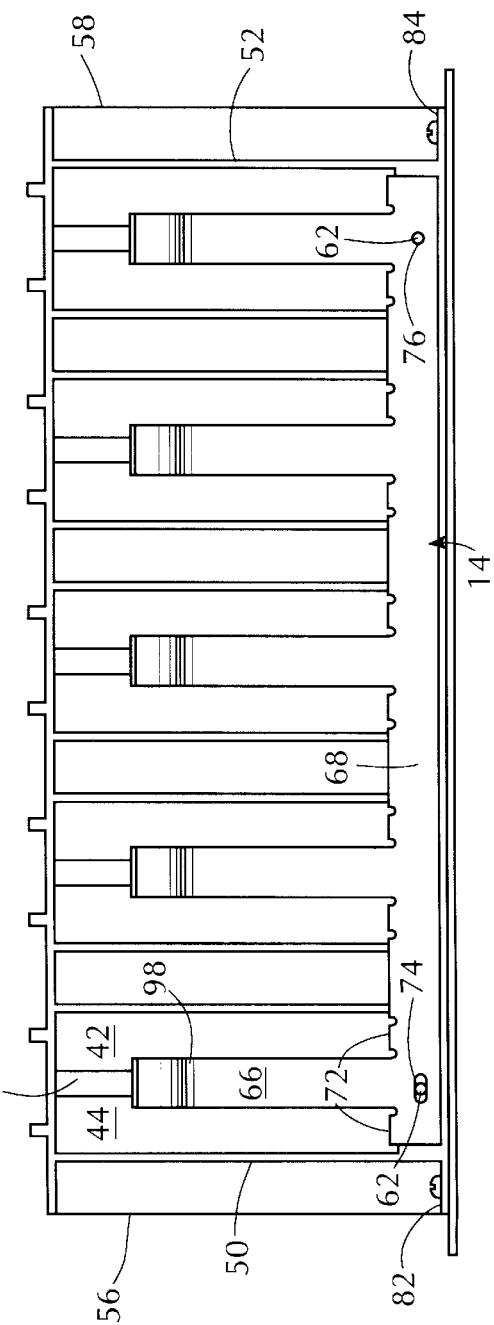

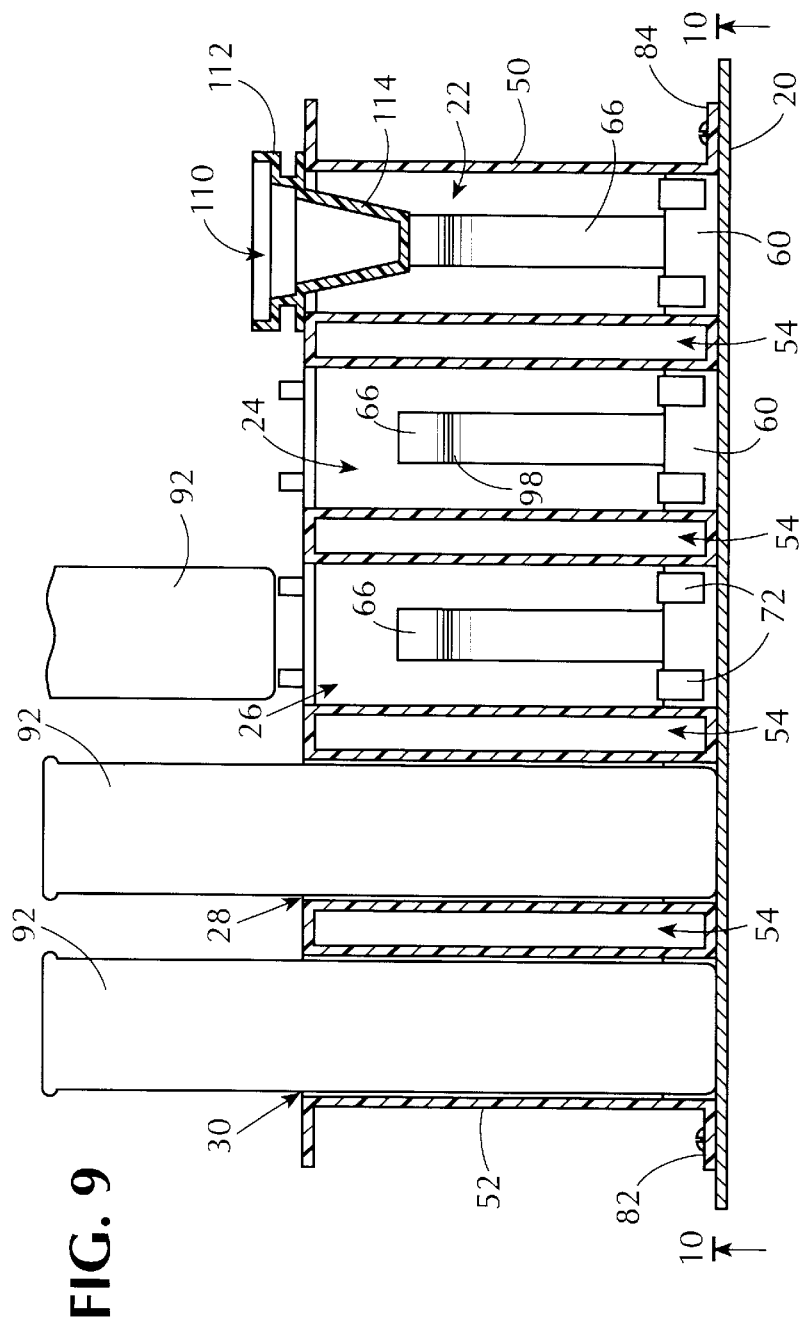
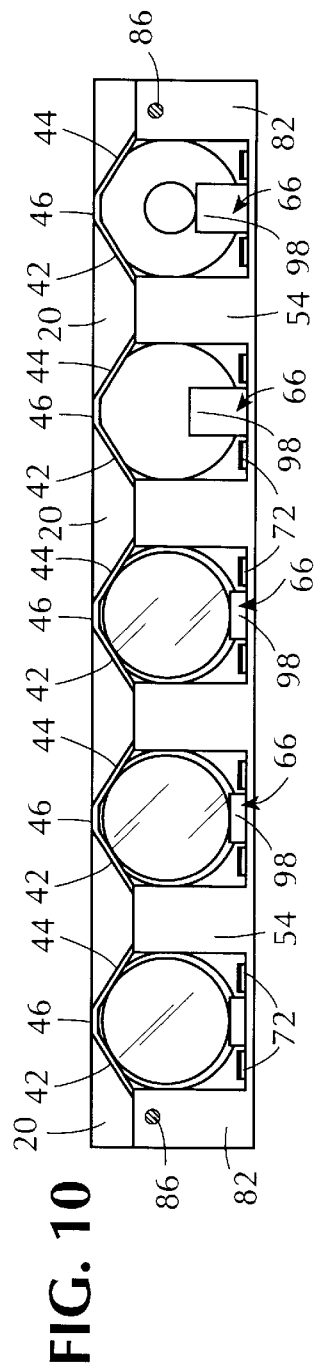
FIG. 9
FIG. 10

SAMPLE TUBE RACK

BACKGROUND OF THE INVENTION

This invention relates to a rack for sample tubes and, more particularly, to a sample tube rack for tubes of different size that can be automatically transported at a rapid rate in a sample analysis system.

In automated sampling systems, sample tubes are usually transported from one location to another in order to conveniently position the tubes for one or more functional operations on the samples contained therein. Because of the demand for increased test output of automated sampling systems, it often becomes necessary to simultaneously transport a plurality of tubes for test purposes.

Although sample tube racks for holding more than one sample tube are known, such racks are often not feasible for automatic transport in a sample analysis system because they can become unstable during movement. As demand increases for high volume test output of sample analysis systems, there has been an emphasis on increasing the speed of processing of the samples within the system. If sample tube racks are used to transport two or more tubes simultaneously, it may be necessary to limit the speed of movement of the rack to assure that the rack remains stable. Also, high speed movement of sample tube racks may necessitate that there be only short time periods during which a rack can be loaded or unloaded. Springs and other detent and holding members within the rack can delay or interfere with the need for quick loading or unloading of tubes relative to the rack.

It is thus desirable to provide a sample tube rack that is stable while undergoing rapid movement within a sample analysis system, permits quick loading and unloading of sample tubes and can accommodate tubes of different size.

OBJECTS AND SUMMARY OF THE INVENTION

Accordingly, it is an object of the invention to provide a novel sample tube rack which can accommodate sample tubes of different size and shape. A further object of the invention is to provide a novel sample tube rack that remains stable while being automatically transported in a sample analysis system. Another object of the invention is to provide a novel sample tube rack which permits quick and easy insertion and removal of sample tubes from the rack. Still another object of the invention is to provide a novel sample tube rack which has as few as two parts, one of which is a plastic housing portion which can be molded in one piece, and the other of which is a biasing spring which can be formed in one piece.

The present invention provides a sample tube rack for holding sample tubes in a single row. The rack includes a rear wall and a top wall that form an angle shaped frame. A plurality of vertical partitions joined to the angle-shaped frame in spaced arrangement define sample tube chambers for receiving sample tubes. At least one front, vertical, connecting section connects the bottom portions of two adjacent partitions opposite the rear wall. A leaf spring device is attached to the connecting section. The leaf spring device includes a support section and a plurality of leaf spring arms which extend upwardly from the leaf spring support section into the tube receiving chambers and are located opposite the rear wall.

The sample tube rack, when anchored to a transport device, can be rapidly transported from one location to another within the sample analysis system. Tubes held by the rack can be easily and quickly loaded into and unloaded from the sample tube chambers of the rack.

BRIEF DESCRIPTION OF THE DRAWINGS

In the accompanying drawings,

FIG. 2 is a rear elevational view thereof;

FIG. 3 is a front elevational view thereof;

FIG. 9 is a sectional view taken on the line 9—9 of FIG. 5; and

FIG. 10 is a sectional view taken on the line 10—10 of FIG. 9.

DETAILED DESCRIPTION

Figure 1:
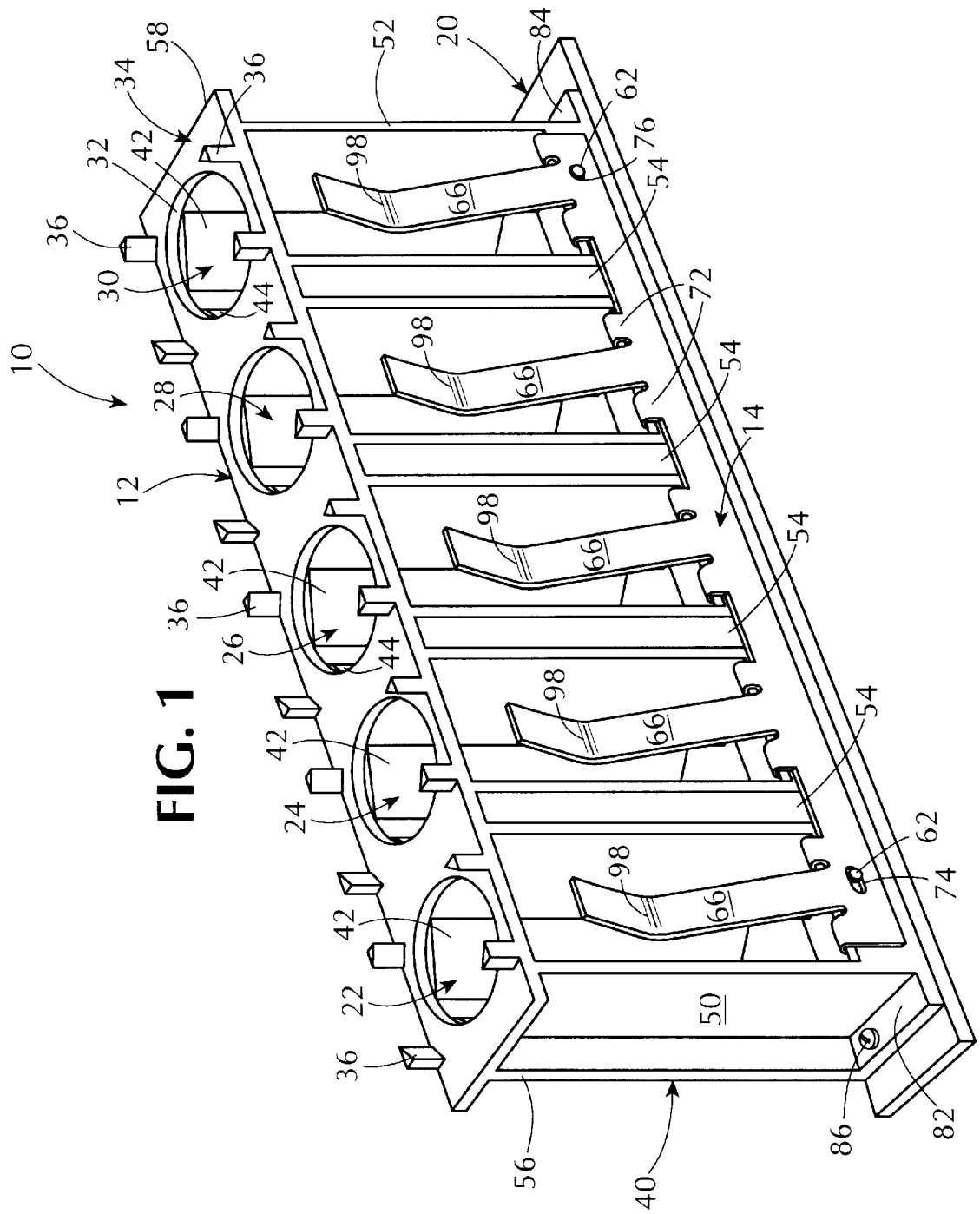
FIG. 1 is a front perspective view of a rack for holding sample tubes incorporating one embodiment of the invention.
Figure 4:
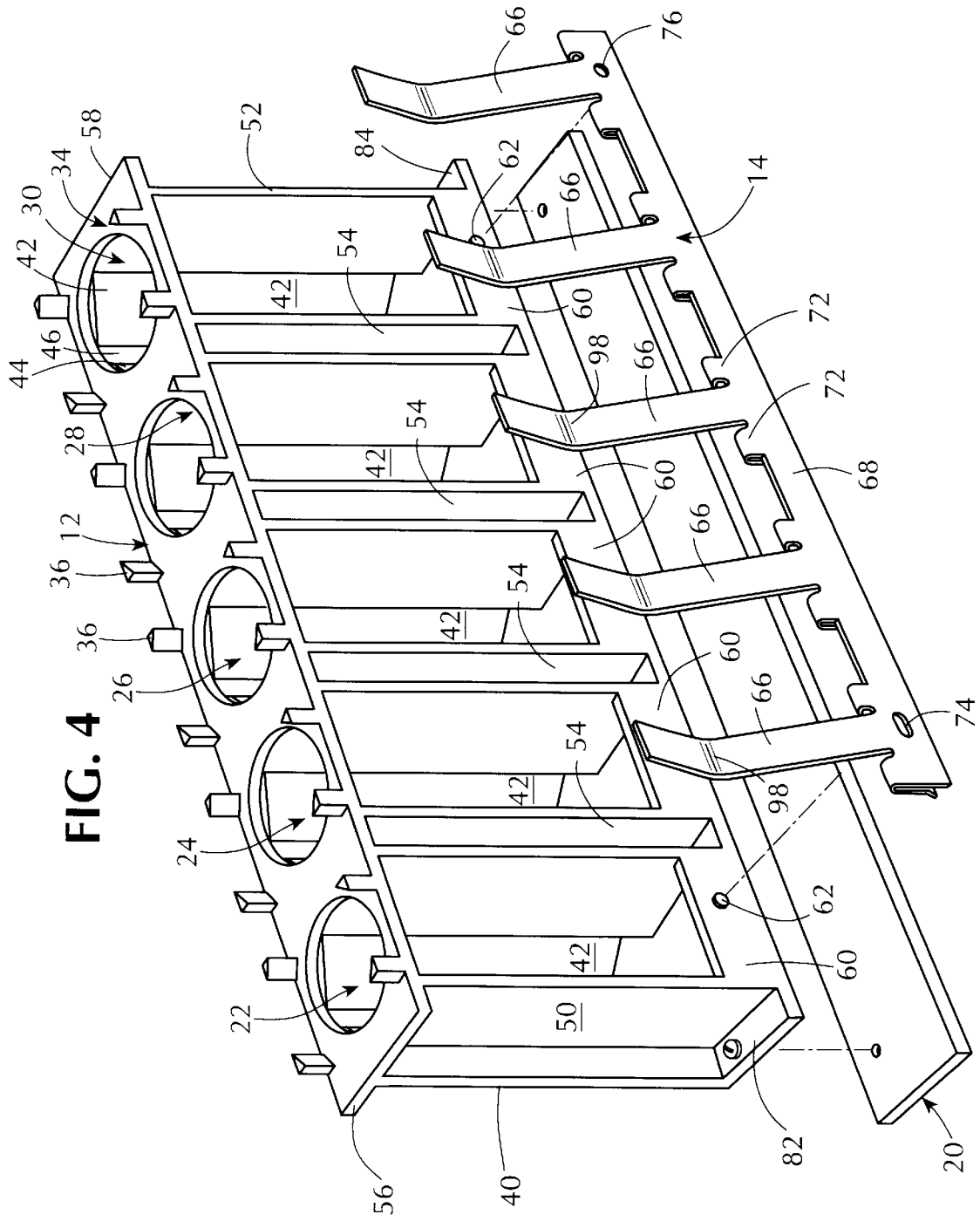
FIG. 4 is an exploded view thereof.

Referring to the drawings, a sample rack incorporating one embodiment of the invention is generally indicated by the reference number 10. Referring to FIGS. 1 and 4, the rack 10 includes a frame or housing shell 12 and a spring component or leaf spring device 14. The rack 10 is supported on a transport plate 20 that is arranged to move the rack and forms no part of the present invention.

The frame 12 includes sample tube chambers 22, 24, 26, 28 and 30 which have chamber openings 32 in an elongated top wall 34. A set of four equally spaced confinement prongs 36 project from the top wall 34 around the periphery of each of the five chamber openings 32.

Figure 5:
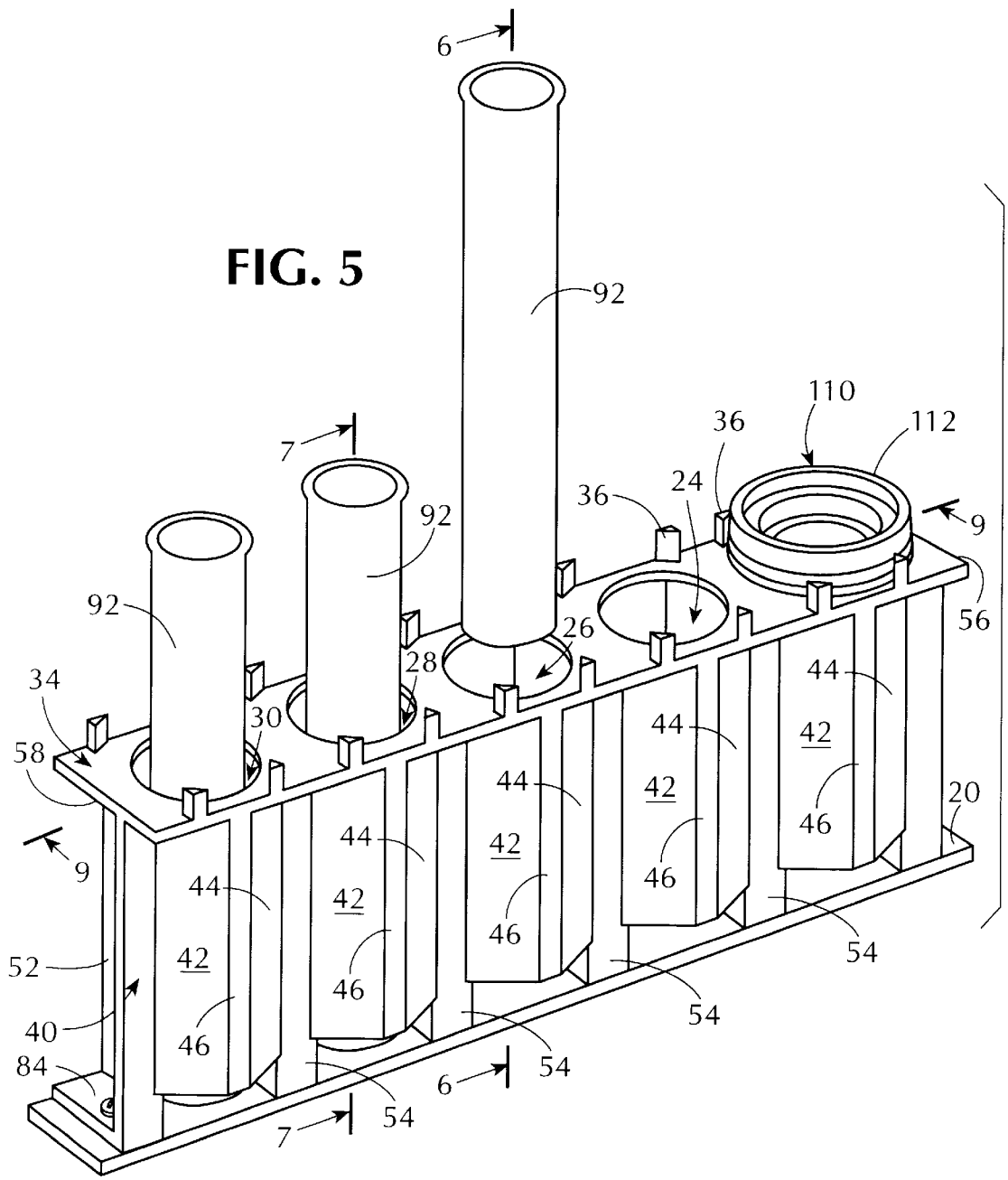
FIG. 5 is a rear perspective view thereof with associated sample tubes.
Figure 6:
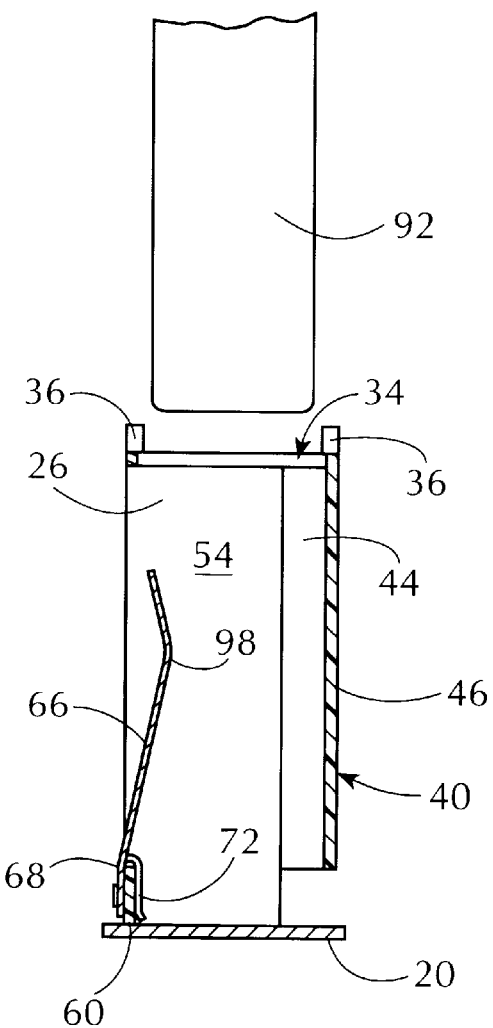
FIG. 6 is a sectional view taken on the line 6—6 of FIG. 5.

A rear wall 40 (FIGS. 2 and 5) depends from the top wall 34 such that the walls 34 and 40 form an upside down "L" or right angle as shown in FIG. 6. The rear wall 40 includes five spaced sets of converging wall sections 42 and 44 that converge to a flat apex section 46. The wall sections 42, 44 and 46 form the back portion of each of the test tube chambers 22, 24, 26, 28 and 30.

As most clearly shown in FIGS. 1 and 4, a small portion of the wall sections 42 and 44 extends within the periphery of the chamber openings 32 such that the wall sections 42 and 44 form contact surfaces for sample tubes 92 (FIG. 5) that can be disposed within the chambers 22, 24, 26, 28 and 30.

The chambers 22, 24, 26, 28, and 30 are set apart from each other by four double wall partitions 54 spaced between end side walls 50 and 52 provided at opposite ends of the rack 10. The end side walls 50, 52 and the partitions 54 extend below the wall sections 42, 44 and 46 as most clearly shown in FIGS. 4 and 5. The end side walls 50 and 52 are slightly recessed from the extreme opposite ends 56 and 58 of the frame 12.

Referring to FIG. 4, a front marginal connecting section 60 is provided at the bottom portion of each chamber 22, 24, 26, 28 and 30. One connecting section 60 with a spring securement pin 62 joins the end side wall 50 and the partition 54 of the chamber 22. Another connecting section 60 with a spring securement pin 62 joins the end side wall 52 and the partition 54 of the chamber 30. Three other connecting sections 60 join the four spaced partitions 54 that form the side walls of the chambers 24, 26 and 28. The connecting sections 60 collectively form a lower front marginal strip of the frame 12.

The spring component 14 includes five spaced spring arms 66 joined at one end to a common leaf spring support section 68. A pair of bent over clips 72 that extend from the support 68 are provided on opposite sides of each leaf spring arm 66. An elongated slot 74 is provided at one end of the support 68 and a round opening 76 is provided at the opposite end of the support.

The spring component 14 is assembled to the frame 12 by engaging the clips 72 onto the connecting sections 60 such that the spring securement pins 62 at the end connecting section 60 are located in the openings 74 and 76 (FIGS. 1 and 3). The clips 72 snugly grip the connecting sections 60. The spring securement pins 62 and the openings 74 and 76 maintain alignment of the spring component 14 on the frame 12 such that each leaf spring arm 66 is aligned with each respective chamber 22, 24, 26, 28 and 30. The leaf spring arms 66 thus extend upwardly in an upside down arrangement and are normally biased a predetermined amount into the chambers 22, 24, 26, 28 and 30.

In using the rack 10, base flange portions 82 and 84 at opposite ends of the rack 10 are secured to the transport plate 20 by any suitable means such as screws 86. The transport plate 20 can function as a floor for the rack 10.

Figure 7:
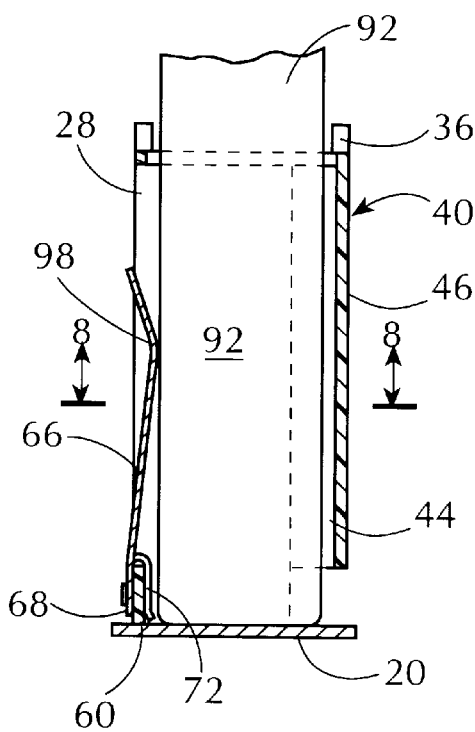
FIG. 7 is a sectional view taken on the line 7—7 of FIG. 5.
Figure 8:
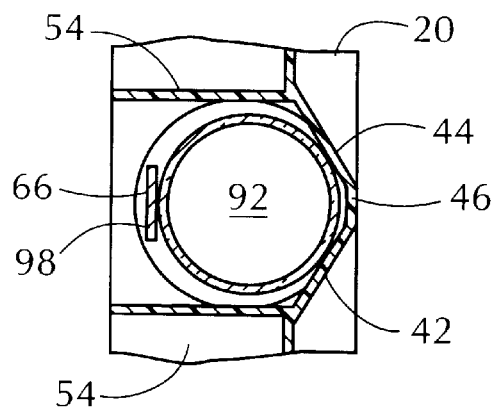
FIG. 8 is a sectional view taken on the line 8—8 of FIG. 7.

Sample tubes such as 92 are disposed in selected chambers such as 26, 28 and 30 (FIG. 5) and engage a bent or contact portion 98 of the biasing spring 66 (FIG. 7) which urge the tubes 92 against the rear wall sections 42 and 44 (FIG. 8). It will be noted that the contact portion 98 is located closer to the free end of the spring 66 than the support section 68. Furthermore the contact portion 98 is positioned to contact the upper half of the sample tube 92 as shown most clearly in FIGS. 7 and 10. Under this arrangement, the force supplied by the springs 66 against the tubes 92 can be predetermined and set to an optimum magnitude that permits easy insertion and removal of sample tubes. Also, the tubes 92 are stabilized in the rack 10 because the detent force supplied by the spring 66 is applied at an upper section of the tube. The tube receiving chambers 22, 24, 26, 28 and 30 can be sized to accommodate tubes of selected length within a predetermined diametrical range of 13–16 millimeters, for example.

The rack 10 can also accommodate relatively small sample tubes 110 (FIGS. 5 and 9), usually referred to as sample cups. The sample cups 110 have a collar portion 112 that fits within the confines of the four prongs 36 that surround the opening 32 of the chamber 22 for example. The cup 110 has a cup portion 114 that depends from the collar 112 into the chamber 22, but not far enough to engage the spring 66.

The rack 10 when secured to the transport plate 20 is maintained in a stable position on the transport plate and moves at the speed of the transport plate. Since the rack 10 is stable when secured to the transport plate 20, the transport plate 20 can provide rapid movement of the rack 10 without upsetting the tubes 92, the sample cups 110 or their contents.

Some advantages of the present invention evident from the foregoing description include a sample rack that accommodates sample tubes of different diameter with a predetermined detent force that permits easy insertion and removal of the sample tubes from the rack. The rack is conveniently secured to a transport plate to permit rapid movement of the rack and its contents without upsetting such contents. The upside down arrangement of the spring and the contact engagement of the spring against the sample tubes at an upper portion of the tube facilitates establishment of a biasing force that permits easy loading and unloading of the rack.

As various changes can be made in the above constructions without departing from the scope of the invention, it is intended that all matter contained in the above description or shown in the accompanying drawings shall be interpreted as illustrative and not an eliminating sense.

What is claimed is:

1. A sample rack for holding sample tubes in a single row, comprising:

an angle shaped frame without a transport plate, said frame having a longitudinally extending, vertical rear wall and a horizontal top wall, said top wall having a plurality of openings;

a plurality of vertical partitions joined to said angle shaped frame in spaced arrangement to define a plurality of tube receiving chambers corresponding to the plurality of openings, each of said partitions having a bottom portion;

at least one front, vertical, connecting section connecting the bottom portions of two adjacent partitions opposite said rear wall; and a spring device having a spring support section, said spring device being attached to said connecting section at said spring support section said spring device including a plurality of leaf spring arms corresponding to the plurality of tube receiving chambers, each of said leaf spring arms extending upwardly into respective said tube receiving chambers from said spring support section and said leaf spring arms also extending upwardly toward said rear wall in respective said tube receiving chambers, and wherein said plurality of leaf spring arms are opposite said rear wall.

2. The rack of claim 1, wherein said partitions are perpendicular to said rear wall.

3. The rack of claim 2, wherein at least one partition is a double wall member.

4. The rack of claim 3, wherein said rear wall includes a plurality of sets of wall sections, each set including a flat apex section and a pair of converging wall sections joined to said flat apex section.

5. The rack of claim 1, wherein the top wall includes a front portion and each of said partitions includes a front portion, and wherein the connecting sections and the front portions of said top wall and said partitions define a plurality of unobstructed openings in the front of said rack.

6. The rack of claim 5, wherein said spring device includes at least one bent clip connected to said spring support section for engaging one of said connecting sections.

7. The sample rack of claim 6, wherein each of said leaf spring arms includes a free end and a bent portion to define a contact point for contacting a sample tube, and wherein the contact point is located closer to the free end of the spring arm than to the spring support section.

8. The rack of claim 1, wherein said leaf spring arms have a free end and a bent portion between said free end and said spring support section, said bent portion engageable against a sample tube when a sample tube of predetermined length is inserted into one of the openings in said top wall.

9. The rack of claim 8, wherein said bent portion is closer to the top wall than the spring support section.

10. The rack of claim 1, wherein said angle shaped frame, said partitions and said connecting section comprise a single, integral body.

11. A sample rack for holding sample tubes in a single row, comprising:

an angle shaped frame without a transport plate, said frame having a longitudinally extending, vertical rear wall and a top wall, said top wall having a plurality of openings;

an end sidewall extending downwardly from each of the opposite ends of the top wall, each of said end sidewalls having a bottom portion;

a plurality of double wall partitions between said end sidewalls, each of said partitions having a bottom portion and each of said partitions connected to said angle shaped frame, wherein one wall from a double wall partition defines a chamber for receiving a sample tube with an opposing wall from an adjacent double wall partition, and wherein each of said end sidewalls defines a chamber for receiving a sample tube with an adjacent wall of a double wall partition;

a plurality of front, vertical, connecting sections opposite said rear wall connecting the bottom portions of adjacent double wall partitions; and a leaf spring device having a spring support section, said spring device being attached to said connecting sections at said spring support section said spring device including a plurality of leaf spring arms corresponding to the plurality of tube receiving chambers, each of said leaf spring arms extending upwardly into respective said tube receiving chambers from said spring support section and said leaf spring arms also extending upwardly toward said rear wall in respective said tube receiving chambers, wherein said plurality of leaf spring arms are opposite said rear wall.

12. The rack of claim 11, wherein said leaf spring device is detachably secured to said connecting sections.

13. The rack of claim 12, wherein one of said connecting sections includes a pin and said leaf spring device includes an opening for engaging said pin.

14. The rack of claim 13, wherein said leaf spring device includes at least one bent clip connected to said leaf spring support section for engaging one of said connecting sections.

15. The rack of claim 14, additionally comprising a plurality of prongs extending upwardly from said top wall and surrounding each of said top wall openings.

* * * * *